(12) United States Patent
Deviere et al.

(10) Patent No.: US 10,010,702 B2
(45) Date of Patent: Jul. 3, 2018

(54) METHOD OF SELECTIVE CATHETERISM OF AN ANATOMICAL STRUCTURE USING A GUIDE

(71) Applicant: UNIVERSITE LIBRE DE BRUXELLES, Brussels (BE)

(72) Inventors: Jacques Deviere, Charleroi (BE); Nicolas Cauche, Brussels (BE); Alain Delchambre, Brussels (BE); Sonia Dugardeyn, Braine le Comte (BE)

(73) Assignee: UNIVERSITE LIBRE DE BRUXELLES, Bruxelles (BE)

( * ) Notice: Subject to any disclaimer, the term of this patent is extended or adjusted under 35 U.S.C. 154(b) by 0 days.

(21) Appl. No.: 15/589,704

(22) Filed: May 8, 2017

(65) Prior Publication Data
US 2017/0266418 A1    Sep. 21, 2017

Related U.S. Application Data

(63) Continuation of application No. 12/866,862, filed as application No. PCT/EP2009/051465 on Feb. 9, 2009, now Pat. No. 9,642,990.

(30) Foreign Application Priority Data

Feb. 7, 2008 (EP) .................... 08151170
Jul. 30, 2008 (EP) .................... 08161434

(51) Int. Cl.
*A61M 25/00* (2006.01)
*A61M 25/09* (2006.01)

(52) U.S. Cl.
CPC ... *A61M 25/09* (2013.01); *A61M 2025/09175* (2013.01)

(58) Field of Classification Search
CPC ........ A61M 25/09; A61M 2025/09175; A61M 2025/09083
(Continued)

(56) References Cited

U.S. PATENT DOCUMENTS 2,024,982 A    12/1934 Scott
4,991,602 A    2/1991 Amplatz et al.
(Continued)

FOREIGN PATENT DOCUMENTS

EP    0 410 557 A2    1/1991
EP    0 515 201 A1    11/1992
(Continued)

OTHER PUBLICATIONS

Lieng-Huang Lee, "Fundamentals of adhesion," Plenum Press New York (1991). ISBN: 0-306-43470-9.

*Primary Examiner* — Daniel Cerioni
(74) *Attorney, Agent, or Firm* — Merchant & Gould P.C.

(57) ABSTRACT

A method of selective catheterism of in a network of conduits of an anatomical structure including inserting a flexible distal end of a guide for catheterism through the network of conduits. An appendage is attached on the distal end of the guide, the appendage includes a channel extending along a longitudinal axis of the guide. A catheter is slid along the catheter until a distal face of the catheter surrounding the guide engages a proximal surface of the appendage. A force oriented in a distal direction is exerted with the catheter on the appendage, which disengages the appendage from the distal end of the guide within the network of conduits. Navigation through the network of conduits is continued with the flexible distal end of the guide once the appendage is removed.

5 Claims, 8 Drawing Sheets

(58) Field of Classification Search
USPC .......................................................... 600/585
See application file for complete search history.

(56) References Cited

U.S. PATENT DOCUMENTS

| | | |
|---|---|---|
| 5,505,686 A | 4/1996 | Willis et al. |
| 5,527,298 A | 6/1996 | Vance et al. |
| 5,755,685 A * | 5/1998 | Andersen ............ A61M 25/104 604/103.04 |
| 5,947,963 A | 9/1999 | Guglielmi |
| 2003/0163064 A1 | 8/2003 | Vrba et al. |
| 2005/0209533 A1* | 9/2005 | Lorenz .................. A61M 25/01 600/585 |
| 2005/0273147 A1 | 12/2005 | Israel |
| 2006/0135949 A1 | 6/2006 | Rome et al. |
| 2008/0051721 A1 | 2/2008 | Carter et al. |
| 2008/0154207 A1* | 6/2008 | Hardin .................. A61M 25/09 604/164.13 |
| 2009/0125007 A1 | 5/2009 | Splinter |

FOREIGN PATENT DOCUMENTS

| | | |
|---|---|---|
| EP | 0 778 042 A2 | 6/1997 |
| EP | 1 092 449 A1 | 4/2001 |
| EP | 1 803 484 A2 | 7/2007 |
| WO | 91/13592 A1 | 9/1991 |
| WO | 94/13350 A1 | 6/1994 |
| WO | 96/00104 A1 | 1/1996 |
| WO | 2004/093659 A2 | 11/2004 |
| WO | 2006/039217 A1 | 4/2006 |
| WO | 2008/024707 A1 | 2/2008 |
| WO | 2008/030737 A2 | 3/2008 |

* cited by examiner

METHOD OF SELECTIVE CATHETERISM OF AN ANATOMICAL STRUCTURE USING A GUIDE

This application is a Continuation of U.S. patent application Ser. No. 12/866,862, filed 3 Nov. 2010, which is a National Stage Application of PCT/EP2009/051465, filed 9 Feb. 2009, which claims the benefit of Ser. No. 08/161, 434.9, filed 30 Jul. 2008 in Europe and which also claims the benefit of Ser. No. 08/151,170.1, filed 7 Feb. 2008 in Europe, and which applications are incorporated herein by reference. To the extent appropriate, a claim of priority is made to each of the above disclosed applications.

OBJECT OF THE INVENTION

The present invention relates to the use of a guide for the selective catheterism of anatomic structures and for placing therapeutic instruments.

BACKGROUND OF THE INVENTION

The passing of a flexible guide called "a guide wire" into the different natural conduits of the human body such as those present in the digestive, hepato-pancreatic, urinary, genital, respiratory, cardiovascular systems is generally necessary for introducing therapeutic instruments ("medical devices") up to the site to be treated. The guide should therefore go through the different conduits with an increasingly reduced width up to the site to be treated. In all these conduits, obstacles may be present preventing proper navigation of the guide and not allowing easy access to said site to be treated. The obstacles may be of different natures, either natural or not, and be formed, for example by the sinuous anatomy of the conduit, or be due to the presence of tumors, calculi, foreign bodies, or further to the presence of folds in the mucosa. In order to navigate in these sinuous and/or obstructed conduits, or to circumvent these obstacles, present guides are provided with a flexible end. Indeed, when the guide is confronted with one of these obstacles, it may be diverted and come to impact or touch the walls of the natural conduit which may cause an injury (edema) and/or with a deterioration of the guide making the continuation of the navigation more difficult. Further, the dimensions of the guide, in particular those of its distal end, opposite to the therapist, should allow navigation of the guide in very narrow conduits, the diameter of which decreases gradually as the guide progresses in the natural routes to be explored.

Solutions have been proposed in the different documents of the state of the art such as the "Loop Tip Wire Guide" described in document WO 2006/039217.

However, the solutions currently present do not allow total resolution of these technical difficulties and therefore do not satisfy the therapists.

SUMMARY OF THE INVENTION

With the present invention, it is possible to navigate in a network of conduits, the diameter of which decreases gradually as the guide progresses in the routes to be explored.

Complementarily, with the present invention, it is possible to avoid injuries or contusions due to the sharp end of the guide, to mucosas and endothelial walls, and the navigation of the guide may be facilitated by means of the particular shape of its end.

According to the invention, a guide for catheterism is proposed, the body of which is provided at its distal end with an appendage or an endpiece having a three-dimensional shape, preferably axisymmetrical around the axis of revolution of said guide. This three-dimensional shape may for example be ovoidal, spheroidal, ellipsoidal. Preferably this shape does not have any edge or acute angle and in particular has a profile perpendicular to the longitudinal axis which has a quasi-constant radius of curvature. By quasi-constant is meant a variation comprised between 50 to 200% and preferably between 75 and 125%.

More particularly, the guide is characterized in that the appendage or endpiece has in the plane perpendicular to the longitudinal axis of said guide body at least one dimension greater than the diameter of said guide body. Preferably, at least one dimension and preferably one dimension in the plane perpendicular to the longitudinal axis and in particular the maximum diameter of the appendage is significantly greater than the diameter of the body of the guide.

By significantly is meant an increase by at least 20%, preferably 30%, preferably 50%, preferably 100%.

According to another alternative, the appendage has significantly greater dimensions than the body of the guide both in the radial and axial directions.

According to a particularly preferred embodiment, the appendage or the endpiece of the guide is detachable from the body of said guide. The dissociation may advantageously occur actually within the human or animal body, i.e. in situ, and preferably on the site to be treated. For this purpose, the presence of dissociation means are provided, which will allow the appendage or the endpiece to be detached or dissociated from the body of said guide on command from the therapist.

Advantageously, dissociation means are provided in order to make the appendage detachable from the guide actually within the human or animal body. This appendage may of course also be detachable outside the human body. As an example, the release of the appendage of the guide may be accomplished by the action of dissociation means already present on the guide.

Dissociation of the appendage or of the endpiece results from voluntary action of the therapist and should not by any means take place suddenly.

Preferably, dissociation is carried out by a mechanical action on command from the therapist.

Means for controlling the dissociation means may also be provided and advantageously allow detachment of the appendage or the endpiece as soon as the site to be treated is reached.

Preferably, the integrality of the appendage or endpiece is detached from the guide so as to avoid the presence of abrasive or blunt portions which may act on the surrounding tissues and injure them.

The attachment of the detachable appendage or endpiece on the guide is carried out preferentially by physico-chemical interactions.

By the terms of "physico-chemical interactions" are meant all the interactions which allow adhesion of two identical or different materials, such as electrostatic, steric, hydration interactions, capillary condensation, interaction due to covalent forces, interaction due to Van der Waals forces, overlapping interactions, etc. ("*Intermolecular & Surfaces*" $2^{nd}$ edition, JACOB ISRAELACHVILI, Academic Press (1992). ISBN: 0-12-375181-0 and "*Fundamentals of adhesion*", LIENG-HUANG Lee. Plenum Press New York (1991). ISBN: 0-306-43470-9).

Preferably, all mechanical interactions are therefore excluded.

Alternatively, the attachment of the appendage or endpiece on the body of the guide is carried out with a substance having adhesive properties.

Advantageously, the connection between the appendage or the endpiece and the body of the guide is selected depending on the physico-chemical properties of the materials used for their respective manufacturing.

According to another particularly preferred embodiment, the material of the appendage or of the endpiece of the guide is advantageously deformable or extensible by deployment.

The material of the appendage or of the endpiece of the guide is advantageously elastic.

According to another embodiment, it is possible to also contemplate that the appendage be not present on the guide before it is introduced into the human body, it only appears in the human body for example by the action of an inflatable membrane.

Alternatively, the material of the appendage or of the endpiece of the guide may not be deformable, this is in particular the case if the endpiece is detachable.

More particularly, this appendage may be made in a metal, organic (for example polymeric, elastomeric), silica, ceramic or composite material. The appendage should be preferably be biocompatible (such as for example as described in the standard EN ISO 10993-1) and unaffected by the surrounding medium.

Preferably, the material in which this appendage or this endpiece is made has a heat expansion coefficient greater than that of the material in which the guide is made.

This appendage may be solid, hollow or crossed by one or more orifices.

Its outer surface will preferably be treated in order to obtain a lower friction coefficient than the anatomic environment and therefore have improved roughness so as to allow and facilitate navigation.

The appendage may be made in the same materials as those used for making the guide.

Preferentially, the body of the guide is made with at least one of the following materials: cellulose acetate, cellulose nitrated, silicon, polyethylene, high density polyethylene, polyethylene terephthalate, polyurethane, polytetrafluoroethylene, polyamide, polyester, polyorthoester, polyvinyl chloride, polypropylene, acrylonitrile-butadiene-styrene, polycarbonate, polyurethane, nylon silicones, polyanhydride and other equivalents.

Preferentially, the appendage or the endpiece is made with at least one of the following materials: cellulose acetate, cellulose nitrate, silicone, polyethylene, high density polyethylene, polyethylene terephthalate, polyurethane, polytetrafluoro-ethylene, polyamide, polyester, polyorthoester, polyvinyl chloride, polypropylene, acrylonitrile-butadiene-styrene, polycarbonate, polyurethane, nylon silicones, polyanhydride or other equivalents.

The present invention advantageously allows single use of the guide for catheter.

BRIEF DESCRIPTION OF THE DRAWINGS

Referring now to the drawings wherein like reference letters and numerals indicate corresponding structure throughout the views.

DESCRIPTION OF SEVERAL PREFERRED EMBODIMENTS OF THE INVENTION

According to a first embodiment, the guide for catheterism is provided at its distal end with an appendage or endpiece having a three-dimensional shape, preferably axisymmetrical, around the axis of revolution of said guide.

Preferably, the guide is characterized in that the appendage or endpiece has in the plane perpendicular to the longitudinal axis of said guide a dimension greater than the diameter of said guide.

Preferably, the appendage of endpiece of the guide is firmly attached to the body of said guide.

Alternatively, the appendage or the endpiece of the guide is detachable from the body of said guide.

Preferably, the material of the appendage or of the endpiece of the guide is deformable.

Alternatively, the material of the appendage or of the endpiece of the guide is not deformable.

FIGS. 1-4 each illustrate a preferential shape of the appendage present at the distal end of the guide. These appendages have a three-dimensional shape and preferably are axisymmetrical around the axis of revolution of the body of the guide. At least one dimension is preferably a dimension in a plane perpendicular to the longitudinal axis and in particular a diameter and preferably the maximum diameter ($\phi_2$) of the appendage 10 is significantly greater than the diameter ($\phi_1$) of the body 1 of the guide.

By significantly, is meant an increase by at least 20% preferably by at least 50% and preferably by at least 100% of the maximum diameter ($\phi_2$) of the appendage 10 relatively to the (constant $\phi_1$) diameter of the body 1 of the guide.

Figure 1:
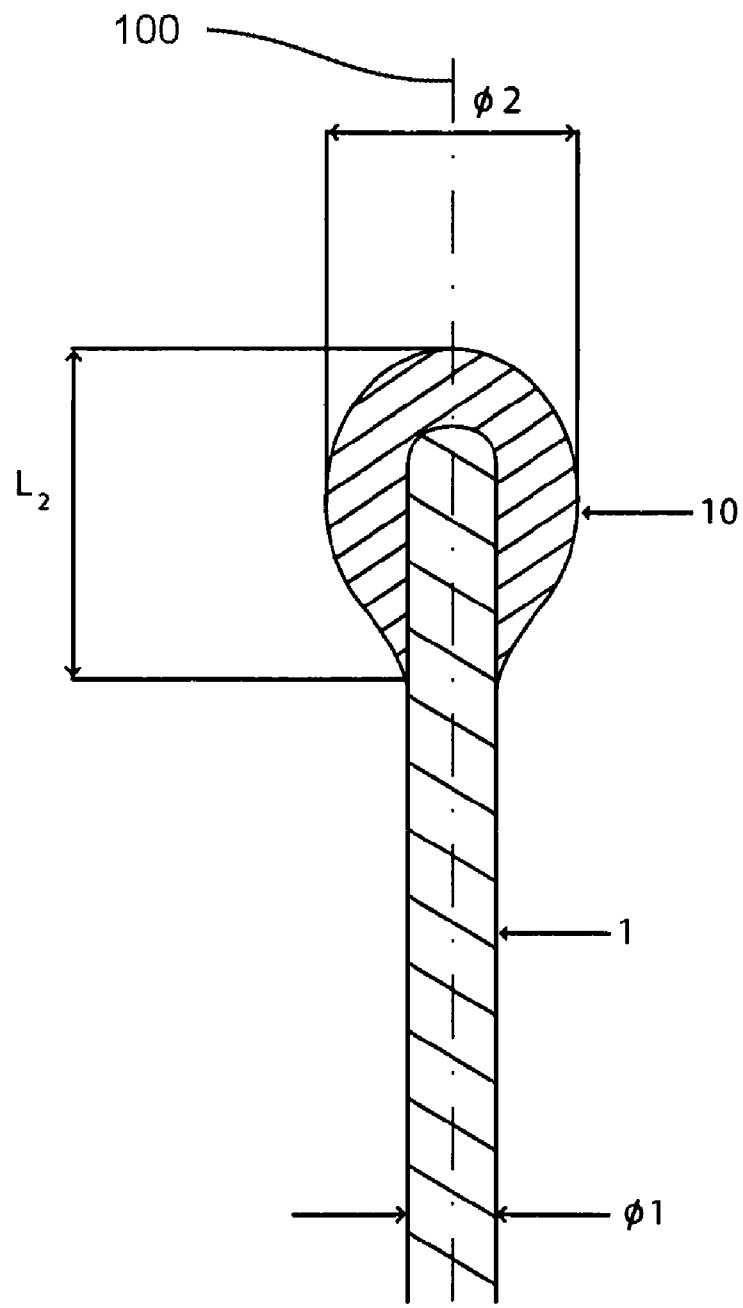
FIG. 1 is a sectional view through an axis of revolution of a first embodiment of an appendage at a distal end of a guide according to the principles of the present invention.

In a first embodiment illustrated in FIG. 1, the appendage significantly juts out from the body 1 of the guide both in the axial direction ($L_2$) and in the radial direction $\phi_2$).

Figure 2:
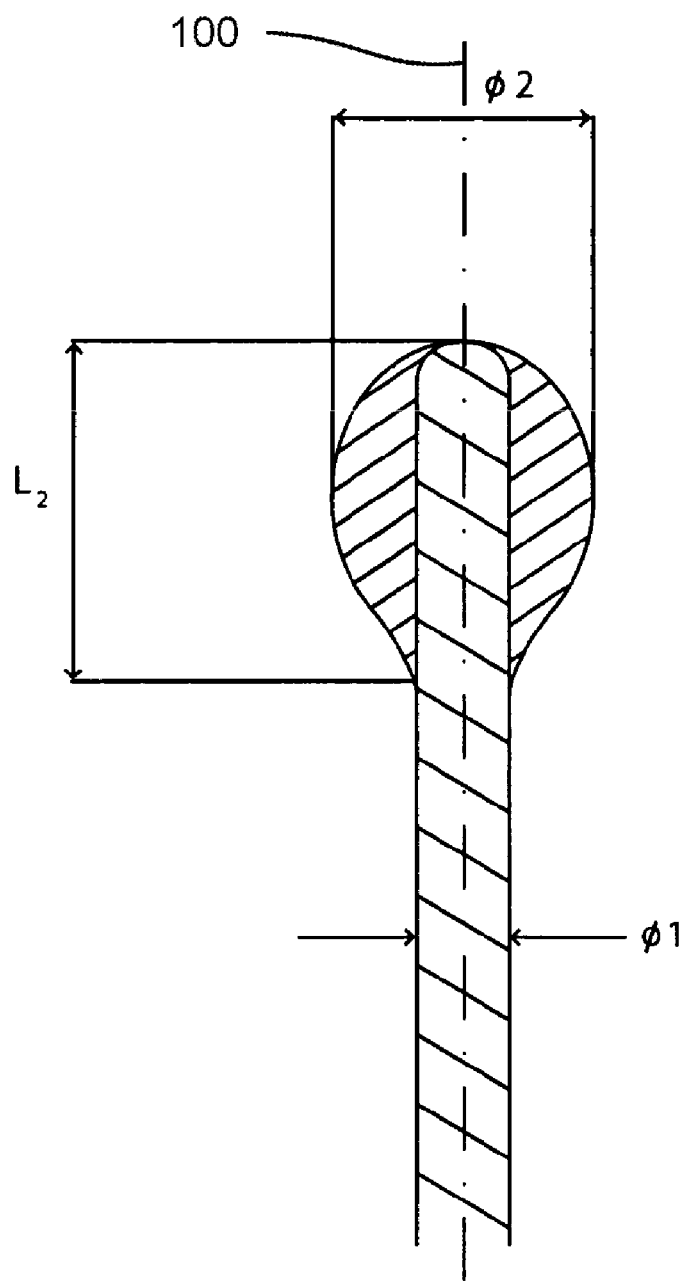
FIG. 2 is a sectional view through an axis of revolution of a second embodiment of an appendage at a distal end of a guide according to the principles of the present invention.
Figure 3:
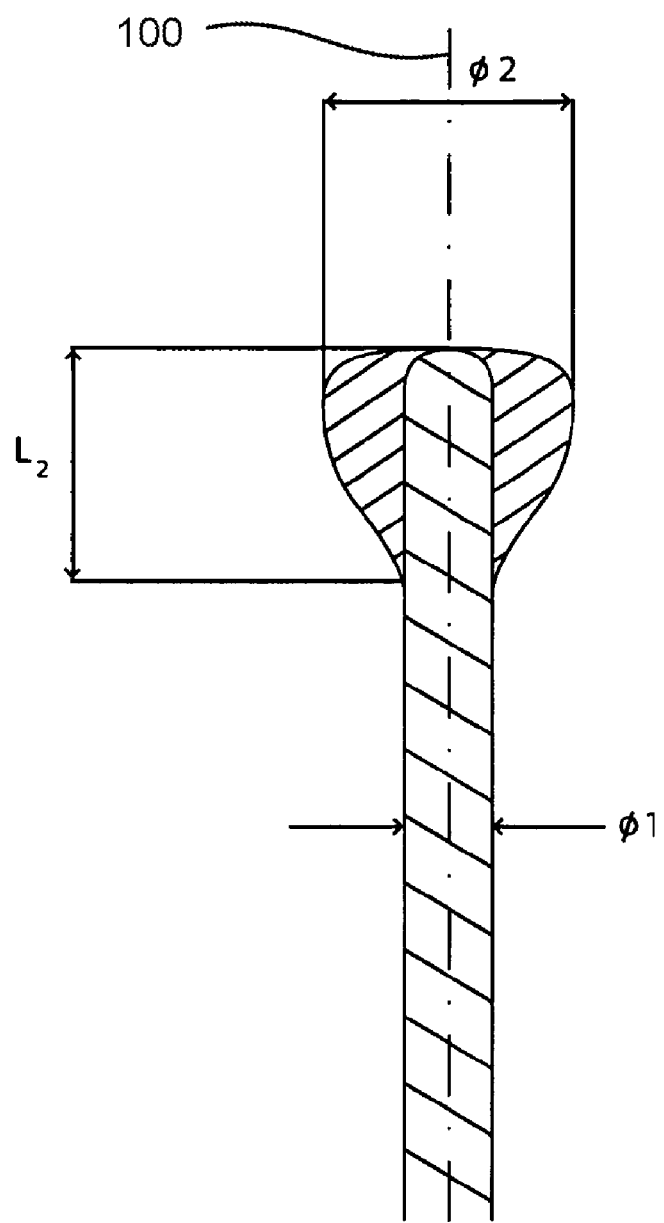
FIG. 3 is a sectional view through an axis of revolution of a third embodiment of an appendage at a distal end of a guide according to the principles of the present invention.

In other embodiments, more particularly illustrated in FIGS. 2 and 3, 1 the dimension (maximal diameter $\phi_2$) of the appendage only significantly exceeds the diameter ($\phi_1$) of the body of the guide 1 in the radial direction. The dimension in the axial direction essentially corresponds to the distal tip of the body of the guide.

Figure 4:
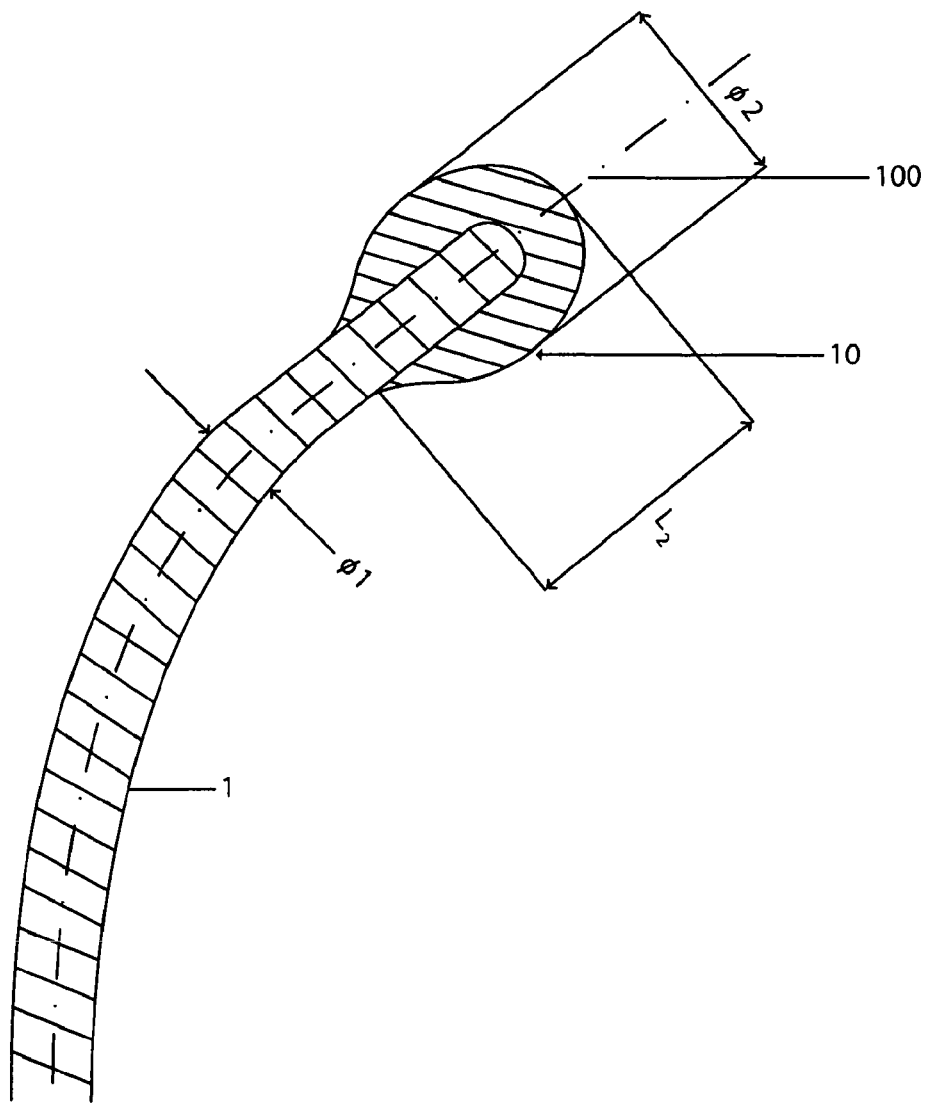
FIG. 4 is a sectional view through an axis of revolution of a curved fourth embodiment of an appendage at a distal end of a guide according to the principles of the present invention.

In another embodiment, more particularly illustrated in FIG. 4, the guide is curved, the axis of revolution of the appendage preferably being the axis 100 of the guide when the latter is straightened out (i.e. in the non-curved position).

Figures 5A, 5B:
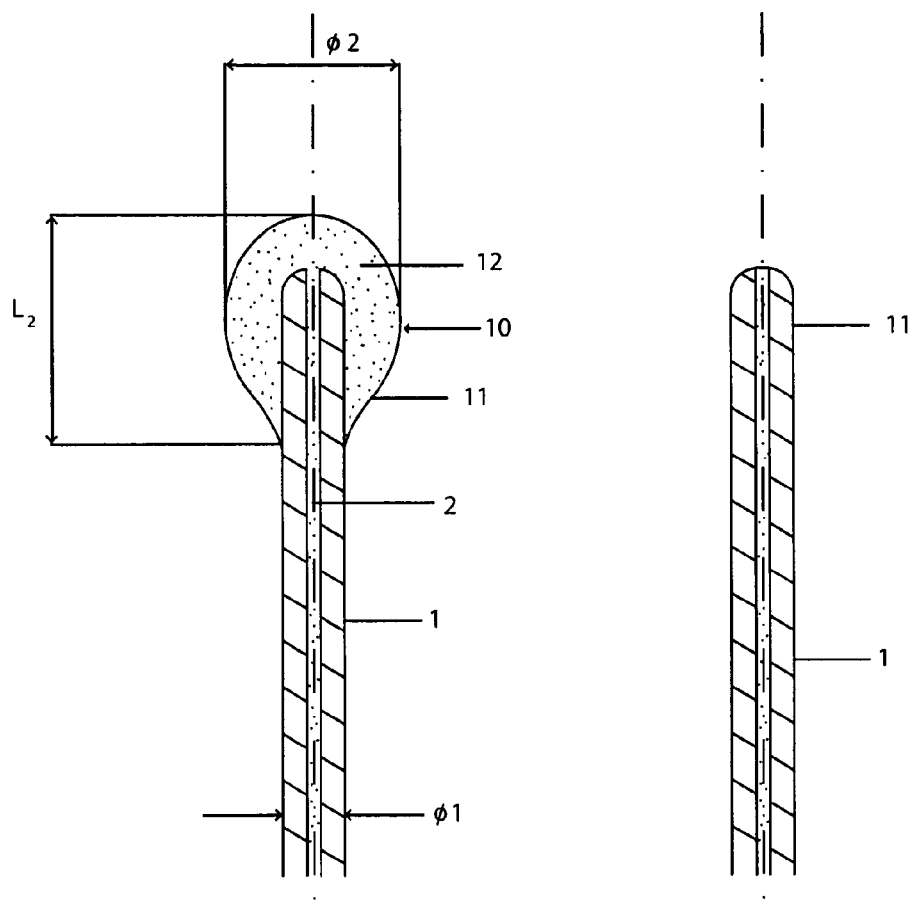
FIG. 5a is a sectional view through an axis of revolution of a fifth embodiment of an appendage at a distal end of a guide according to the principles of the present invention.
FIG. 5b is a sectional view through the axis of revolution showing the embodiment of FIG. 5a with the appendage inflated.

In another embodiment as the one illustrated in FIG. 5, the appendage is deformable or extensible allowing a change in shape and/or in volume, allowing a transition from a non-deployed state to a deployed state or vice versa, the deployed state being defined by the fact that at least one dimension and in particular one dimension perpendicular to the longitudinal axis, and preferably the diameter ($\phi_2$) of the appendage, is significantly greater than the diameter ($\phi_1$) of the body of the guide while the non-deployed state corresponds to a state where the appendage does not have any dimension in the plane perpendicular to the longitudinal axis, greater than the maximum dimension and in particular than the diameter of the body of the guide.

In this particularly preferred embodiment of the invention, the appendage 10 is preferentially formed by an extensible or inflatable element 11 such as a membrane or a balloon, which may be inflated by a gas or a fluid 12.

In this case, the volume of the appendage 10 is for example obtained by simply injecting a pressurized fluid through an internal channel 2 present in the guide 1.

Figures 6A, 6B:
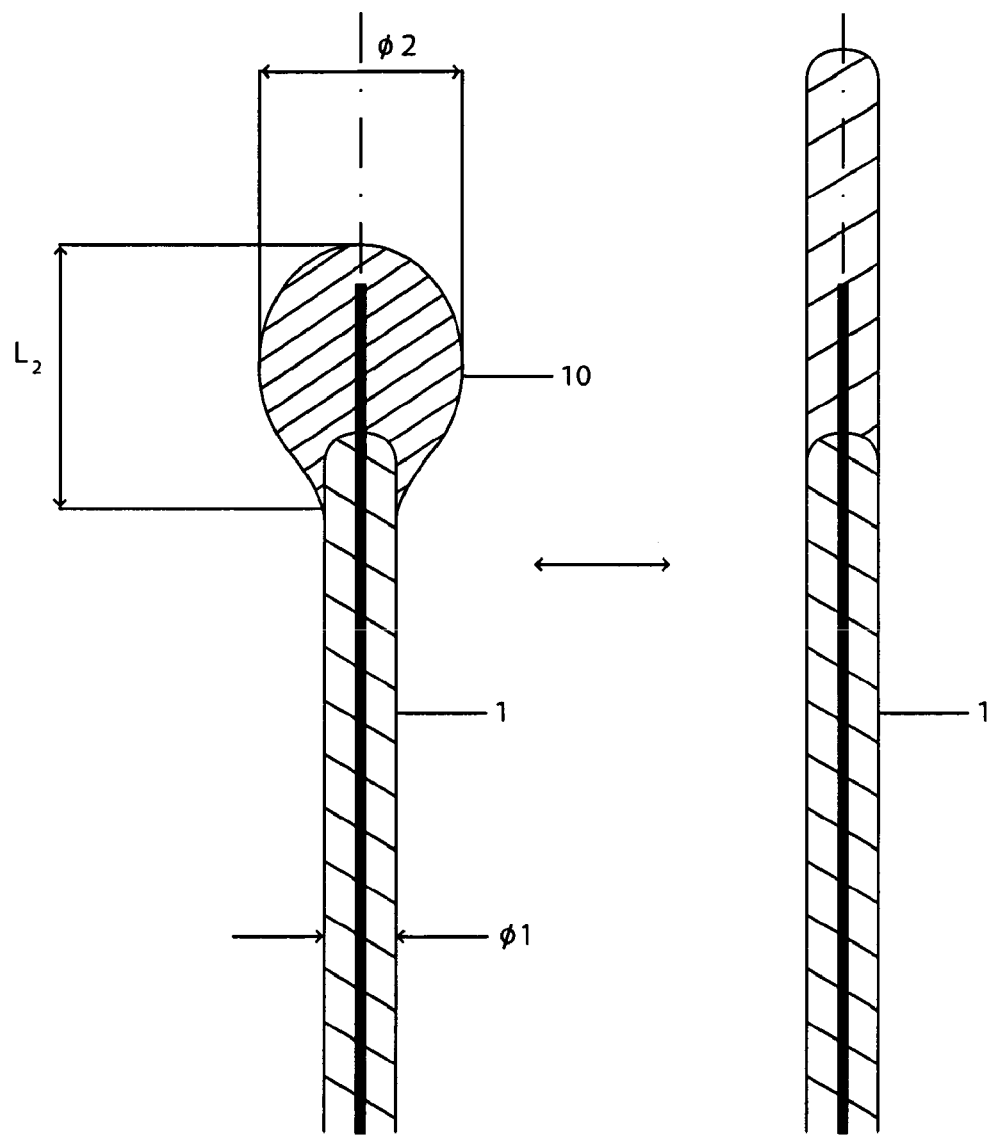
FIG. 6a is a sectional view through an axis of revolution of a sixth embodiment of an appendage at a distal end of a guide according to the principles of the present invention.
FIG. 6b is a sectional view through the axis of revolution showing the embodiment of FIG. 6a with the appendage extended.

According to an embodiment illustrated in FIG. 6, the appendage 10 is extensible or deformable. By extensible, is meant a change in volume of the appendage while by deformable is meant a change in its shape.

Advantageously, the appendage may pass from a deployed state to a non-deployed state by modification of its shape and/or of its volume. The deployed state is defined by the fact that at least one dimension and in particular one dimension perpendicular to the longitudinal axis of the body of the guide and preferably the maximum diameter of the appendage is significantly greater than the diameter of the volume of the guide while the non-deployed state corresponds to a state where the appendage does not have any dimension greater than the diameter of the body of the guide.

According to another preferred embodiment, the appendage may be made in a shape memory material such as shape memory polymers which will modify their state or their shape by a rise in the temperature of the ambient medium. This rise in temperature may quite simply occur by application of an external means such as an electric current or simply by the influence of the body temperature.

Figure 7A:
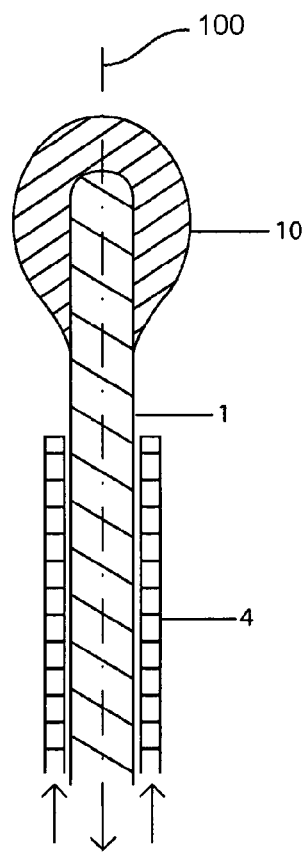
FIG. 7a-7c are sectional views through the axis of revolution showing the embodiment of FIG. 1 with a catheter and showing the steps in removing the appendage.
Figure 7B:
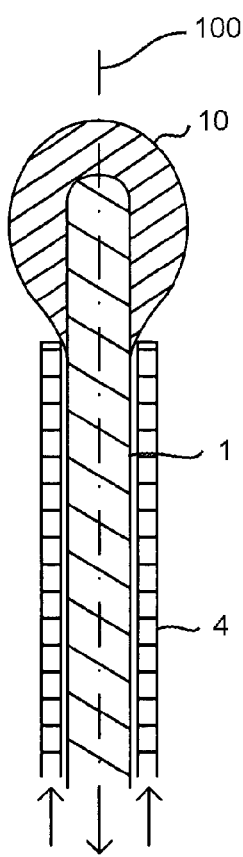
Figure 7C:
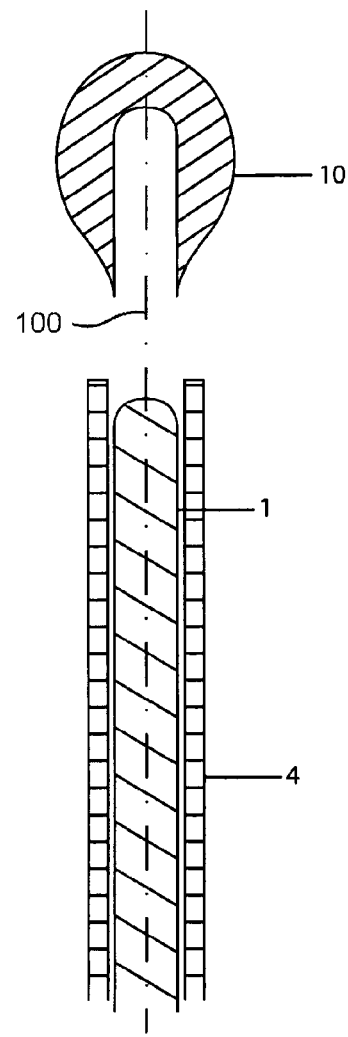

FIG. 7 illustrate the means for detaching or dissociating the appendage 10 or the endpiece (detachable) from the body of the guide 1. The different steps (FIGS. 7a-7c) required for detaching the appendage or the endpiece from said means are illustrated therein.

The dissociation means illustrated in FIG. 7 are for example formed by a catheter 4 which exerts pressure on the outer face of the appendage 10 or of the endpiece.

Preferably, the end of the catheter exerting this pressure comprises a ring or circlet ensuring uniform distribution of the pressure on the appendage or the endpiece. Preferably, the presence of this ring increases the stiffness of the end of the catheter.

Figure 8A:
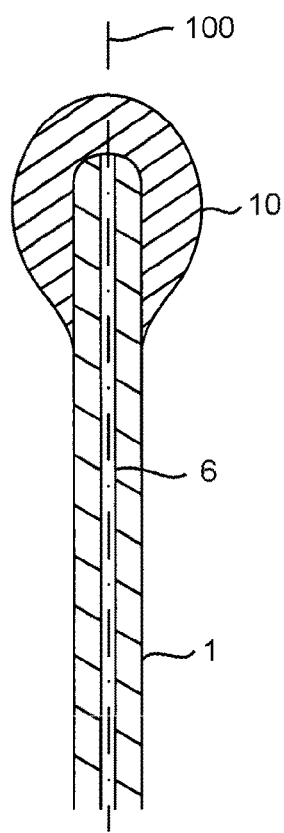
FIG. 8a-8c are sectional views through the axis of revolution showing the embodiment of FIG. 1 showing the steps in removing the appendage.
Figure 8B:
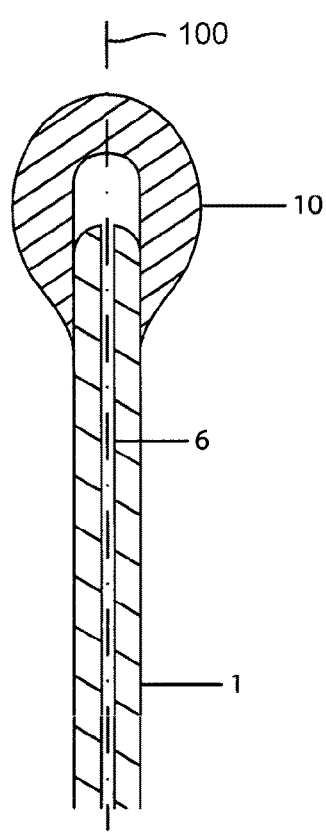
Figure 8C:
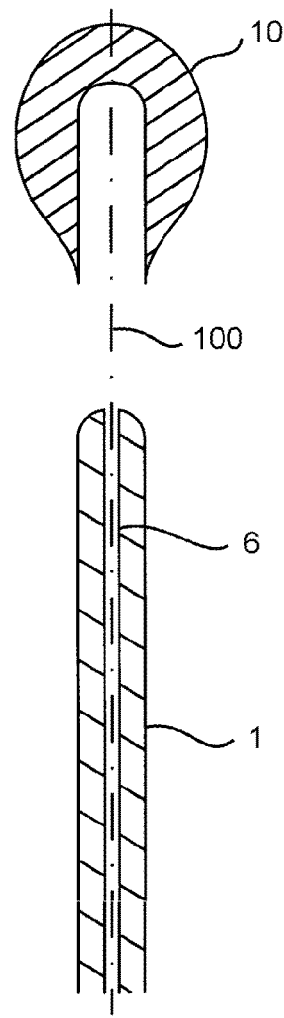

FIG. 8 illustrate means for detaching or dissociating the appendage 10 or the endpiece (detachable) from the guide body 1. The different steps (FIGS. 8a-8c) required for detaching the appendage or the endpiece with said means are illustrated therein.

The firm attachment means illustrated in FIG. 8 are formed by an internal conduit or channel 6 present inside the guide body 1 and one of the open ends of which coincides with the distal end, relatively to the therapist, of the guide.

This conduit or channel 6 allows a pressurized fluid to be conveyed from the proximal end, relatively to the therapist, of the guide.

This fluid will exert sufficient pressure on the internal face of the appendage 10 or endpiece so as to cause its integral dissociation from the guide 1.

Preferably, this fluid is a liquid. Alternatively, this fluid is a gas. Preferably, this liquid is water. Alternatively, this liquid is a saline buffer.

A device comprising both types of aforementioned means for detaching the detachable appendage or endpiece from the guide is another preferred embodiment.

EXAMPLES

1. Selective Catheterism of the Biliary Route.

Selective catheterism of the biliary route through the papilla of Vater is technically difficult and may be accomplished either directly with a catheter or with a guide. Oddi's sphincter is covered with a mucosa and, when catheterism is not successful during the first maneuvers, repeated handling of catheters or of a guide which impacts in the mucosa, creates an edema, making the procedure more difficult.

The type of guide described above, provided with an atraumatic and rounded end, not having any angulation, allows reduction of the trauma of the mucosa and of the edema resulting from this. Also, it helps the flexible end of the guide to adapt to the S-shape of the papilla, in order to find its way towards the biliary route.

Guides modified according to the present invention have been tested in animal models. These tests have revealed that this particular embodiment of the present invention allows significant reduction in the tendency to impaction of the distal end of the guide in a complex structure.

In order to be able to continue to use the guide, in narrower conduits, the appendage is voluntarily detached from the guide, inside the animals by action of the catheter on the guide.

The appendage used for this catheterism is a shape similar to the one illustrated in FIG. 2. This appendage is detached from the body of the guide by action of the dissociation means. The tested material forming the appendage is polyester. The dimensions of appendage for this test are:

$\phi_1$: diameter of the guide, at its flexible end.
$\phi_1$=0.035" (0.889 mm) in this example.
$\phi_2$=maximum diameter of the appendage.
$\phi_2$=1.7 mm in this example.
$L_2$: height of the appendage.
$L_2$=2.5 mm in this example.

2. Selective Catheterism of the Pancreas.

Selective catheterism of the pancreas is technically difficult and may be accomplished either directly with a catheter, or with a guide. Oddi's sphincter is covered with a mucosa and when the catheterism is not successful during the first maneuvers, repeated handling of catheters or a guide which impacts in the mucosa, creates an edema, making the procedure more difficult. The type of guide described above, provided with an atraumatic and rounded end, not having any angulation, allows reduction of the trauma at the mucosa and of the edema resulting from this. Also, it helps the flexible end of the guide to adapt to the S-shape of the papilla, in order to find its way towards the pancreas.

Guides modified according to the present invention have been tested in animal models. These tests have revealed that this particular embodiment of the present invention allows significant reduction in the tendency to impaction of the distal end of the guide in complex structures.

The appendage used for this catheterism is a spherical shape. The tested material forming the appendage is polyester. The dimensions of the appendage for this test are:

$\phi_1$: diameter of the guide, at its flexible end.
$\phi_1=0.035''$ (0.889 mm) in this example.
$\phi_2$=maximum diameter of the appendage.
$\phi_2=1.5$ mm in this example.
$L_2$: height of the appendage.
$L_2=1$ mm in this example.

Dimensions of the Appendage in the Case of Catheterism of the Biliary Route and of the Pancreas:

$1.2\phi_1 < \phi_2 < 3$ mm
$0.5$ mm $< L_2 < 5$ mm
$\phi_2$: diameter of the guide at its flexible end.
$\phi_2$: maximum diameter of the appendage.
$L_2$: height of the appendage.

The invention claimed is:

1. A method of selective catheterism of an anatomical structure, the anatomical structure comprising a network of conduits, the method comprising:
    attaching an appendage on a distal end of a guide for catheterism, the guide having a longitudinal axis and a proximal end opposite the distal end, wherein the distal end of the guide is flexible and comprises a first diameter; the appendage having a three-dimensional shape, the shape comprising a second diameter larger than the first diameter, wherein the appendage comprises a channel extending along the longitudinal axis;
    wherein the distal end of the guide comprises a portion having a continuous diameter, the portion comprising the first diameter and extending along the longitudinal axis, wherein the appendage is attached on the distal end of the guide so that a distal part of the portion having a continuous diameter extends in the channel and a proximal part of the portion having a continuous diameter extends from the distal part outward beyond the channel towards the proximal end of the guide;
    inserting the distal end of the guide and the appendage through the network of conduits;
    sliding a catheter along the proximal part of the portion having a continuous diameter until a distal face of the catheter surrounding the guide engages a proximal surface of the appendage and the appendage blocks further movement of the catheter in a distal direction;
    exerting with the catheter a force oriented in the distal direction on the appendage and disengaging the appendage from the distal end of the guide within the network of conduits;
    continuing navigation through the network of conduits with the flexible distal end of the guide once the appendage is removed.

2. The method of claim 1, wherein the catheter comprises an axial lumen and the proximal part of the portion having a continuous diameter is received in the axial lumen, wherein the axial lumen has a diameter smaller than the second diameter.

3. The method of claim 1, wherein the distal face of the catheter is ring-shaped and surrounds the guide.

4. The method of claim 1, wherein the anatomical structure is the biliary route and the distal end of the guide is inserted through papilla of Vater.

5. The method of claim 1, wherein the anatomical structure is the pancreas and the distal end of the guide is inserted through the sphincter of Oddi.

* * * * *